United States Patent

Ohno et al.

[11] Patent Number: 5,886,234
[45] Date of Patent: Mar. 23, 1999

[54] PROCESS FOR PRODUCING CYCLIC UNSATURATED ALDEHYDES

[75] Inventors: Takashi Ohno, Tokyo; Toshiyuki Tsubouchi, Sodegaura, both of Japan

[73] Assignee: Idemitsu Kosan Co., Ltd., Tokyo, Japan

[21] Appl. No.: 973,555

[22] PCT Filed: Jun. 21, 1996

[86] PCT No.: PCT/JP96/01720

§ 371 Date: Dec. 22, 1997

§ 102(e) Date: Dec. 22, 1997

[87] PCT Pub. No.: WO97/00844

PCT Pub. Date: Jan. 9, 1997

[30] Foreign Application Priority Data

Jun. 22, 1995 [JP] Japan .................................. 7-155732

[51] Int. Cl.⁶ .................................................. C07C 45/45
[52] U.S. Cl. ........................................... 568/445; 568/460
[58] Field of Search ...................... 568/460, 445

[56] References Cited

U.S. PATENT DOCUMENTS 4,992,416  2/1991  Bruns ........................................ 512/16

FOREIGN PATENT DOCUMENTS 7-188092 A  7/1995  Japan .

OTHER PUBLICATIONS

Lucchetti et al, Tetrahedron Letters, 25(39), 1984.
Kelly et al, Tetrahedron Letters, vol. 30, pp. 1357–1360, 1989.
Olson et al, Tetrahedron Letters, vol. 32, pp. 5299–5302, 1991.
Catieviela et al, Tetrahedron, vol. 49, pp. 4073–4084, 1993.

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

A process for producing a cyclic unsaturated aldehyde is herein disclosed which comprises the step of reacting a cyclic conjugated diene compound with an aldehyde represented by the general formula (I)

$$R\text{—}CH\text{=}CH\text{—}CHO \qquad (I)$$

wherein R is an alkyl group having 1 to 3 carbon atoms, in the presence of a solid acid catalyst in accordance with the Diels-Alder reaction.

According to the process of the present invention, the cyclic unsaturated aldehydes useful as the raw materials of traction oils and the like can efficiently and industrially advantageously be produced through the Diels-Alder reaction at a low cost without causing the corrosion of an apparatus and without requiring any treatment after the reaction.

10 Claims, No Drawings

PROCESS FOR PRODUCING CYCLIC UNSATURATED ALDEHYDES

This is the U.S. National Stage Application of PCT/JP96/01720 filed Jun. 21, 1996 now WO97/00844 published Jan. 9, 1997.

TECHNICAL FIELD

The present invention relates to a process for producing cyclic unsaturated aldehydes, and more specifically, it relates to a process for efficiently producing cyclic unsaturated aldehydes useful as the raw materials of traction oils and unsaturated polyester resins, modifiers for phenolic resins, and functional chemical products such as monomers for functional resins through the Diels-Alder reaction at a low cost without causing the corrosion of an apparatus and without requiring any treatment after the reaction.

BACKGROUND ART

Cyclic unsaturated aldehydes are compounds which are useful as the raw materials of traction oils and unsaturated polyester resins, modifiers for phenolic resins, and functional chemical products such as monomers for functional resins.

On the other hand, a fluid for traction drive is used in a traction drive device (a friction drive device by rolling contact), for example, a continuously variable transmission for a car or a continuously variable transmission for an industry, and such a fluid requires a high traction coefficient, stability to heat and oxidation, and economy. economy.

Known examples of the fluid for the traction drive include hydrocarbon compounds having a norbornane skeleton such as 2-formyl-methylbicyclo[2,2,1]hepta-5-ene and 2-formyl-dimethylbicyclo[2,2,1]hepta-5-ene in which cyclic unsaturated aldehydes are intermediates for synthesis (Japanese Patent Application Laid-open No. 95295/1991), and hydrocarbon compounds having a bicyclooctane skeleton such as 2-formyl-methylbicyclo[2,2,2]octa-5-ene and 2-formyl-dimethylbicyclo[2,2,2]octa-5-ene in which cyclic unsaturated aldehydes are intermediates for synthesis (Japanese Patent Application Laid-open No. 9134/1993).

The above-mentioned 2-formyl-methylbicyclo[2,2,2]-hepta-5-ene or 2-formyl-dimethylbicyclo[2,2,2]hepta-5-ene can generally be obtained by reacting cyclopentadiene or methylcyclopentadiene with crotonaldehyde in accordance with the Diels-Alder reaction, and the above-mentioned 2-formyl-methylbicyclo [2,2,2]octa-5-ene or 2-formyl-dimethylbicyclo-[2,2,2]octa-5-ene can generally be obtained by reacting 1,3-cyclohexadiene or methyl-1,3-cyclohexadiene with crotonaldehyde in accordance with the Diels-Alder reaction. If no catalyst is used in such a Diels-Alder reaction, a high temperature of 100° C. or more is required, because crotonaldehyde is less reactive. As a result, polymers of the cyclic conjugated diene compound and crotonaldehyde which are the starting materials are formed, or heavy compounds are formed by the further addition of the diene compound to the desired product, so that a yield of the desired product deteriorates inconveniently. As the catalysts for the Diels-Alder reaction, for example, Lewis acids such as titanium tetrachloride and ethylaluminum dichloride are heretofore known, but since they are liquid, a post-treatment is necessary after the reaction, and they are liable to corrode an apparatus. Therefore, they are not suitable for industrial production. In consequence, it has been demanded to develop a catalyst which does not require the post-treatment and which has no corrosive properties.

With regard to the Diels-Alder reaction of crotonaldehyde and cyclopentadiene, there has been reported an embodiment in which the reaction is carried out at 100° C. for 4 hours without using any catalyst ["Ann.", Vol. 470, p. 62, (1929)]. However, the above conditions lead to the formation of large amounts of by-products such as a polymer of the cyclopentadiene and crotonaldehyde, and a condensate in which 2 mol of cyclopentadiene is added to crotonaldehyde, with the result that the selectivity of the desired product is low.

On the other hand, as reaction embodiments using the catalyst, there have been reported an embodiment in which the reaction is carried out at −78° C. for 1.5 hours in the presence of a catechol boron bromide catalyst (yield=70%), an embodiment in which the reaction is carried out at −78° C. for 1 hour by the use of a ferrocenium hexafluorophosphate catalyst (yield=78%) ["Tetrahedron Letters", Vol. 30, p. 1357 (1989)], and an embodiment in which the reaction is carried out at −78° C. for 1 hour in the presence of a 2-chloro-1,3,2-dithiaborane catalyst (yield=72%) ["Tetrahedron Letters", Vol. 34, p. 4095 (1993)]. In these methods, however, the homogeneous reaction is done at a low temperature in the presence of the expensive catalyst by the use of the solvent, and hence they cannot industrially be applied at all.

With regard to the Diels-Alder reaction using a heterogeneous solid catalyst, there are known an embodiment in which cyclopentadiene is reacted with acrolein, acrylic acid or acrylonitrile in the presence of silica, alumina or a cellulose catalyst ["Angew. Chem.", Vol. 93, p. 1114 (1981)], an embodiment in which cyclopentadiene is reacted with crotonic acid in the presence of a silica catalyst or an alumina catalyst ["Anorg. Chem.", Org. Chem., Vol. 36B, p. 898 (1981)], an embodiment in which safflower oil is reacted with maleic anhydride in the presence of a silica-alumina catalyst ["Oil Chemistry", Vol. 27, p. 435 (1978)], and an embodiment in which methylcyclopentadiene is reacted with maleic anhydride in the presence of a catalyst such as silica-alumina, silica-magnesia, alumina-boria, active terra abla, solid phosphoric acid or a cation exchange resin (Japanese Patent Application Laid-open No. 73043/1994). However, a specific technique is not known so far in which the cyclic conjugated diene compound is reacted with an aldehyde having a lower alkyl group at the third position of an acrolein such as crotonaldehyde in the presence of a solid acid catalyst in accordance with the Diels-Alder reaction.

DISCLOSURE OF THE INVENTION

An object of the present invention is to provide an industrially advantageous process for efficiently producing a cyclic unsaturated aldehyde at a low cost without causing the corrosion of an apparatus and without requiring any treatment after reaction by reacting a cyclic conjugated diene compound with an aldehyde having a lower alkyl group at the third position of an acrolein in accordance with the Diels-Alder reaction under the above-mentioned circumstance.

The present inventors have intensively researched with the intention of achieving the above-mentioned object, and as a result, it has been found that the above-mentioned object can be achieved by using a solid acid catalyst as a catalyst. The present invention has been completed on the basis of this finding.

That is to say, the present invention is directed to a process for producing a cyclic unsaturated aldehyde which comprises the step of reacting a cyclic conjugated diene compound with an aldehyde represented by the general formula (I)

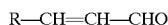  (I)

wherein R is an alkyl group having 1 to 3 carbon atoms, in the presence of a solid acid catalyst in accordance with the Diels-Alder reaction.

BEST MODE FOR CARRYING OUT THE INVENTION

In a process of the present invention, the ring of a cyclic conjugated diene compound which can be used as one of materials preferably has 5 to 20 carbon atoms, and more preferably, the ring has 5 or 6 carbon atoms from the viewpoints of the easiness of availability, reactivity, the usefulness of an obtained product and the like. Furthermore, this cyclic conjugated diene compound may have a suitable substituent on the ring, and examples of the substituent include lower alkyl groups such as a methyl group, an ethyl group, an n-propyl group and an isopropyl group, lower alkoxy groups such as a methoxy group, an ethoxy group, an n-propoxy group and an isopropoxy group, and halogen atoms such as a chlorine atom, a fluorine atom and a bromine atom. One or more of these substituents may be introduced into the cyclic conjugated diene compound.

Preferable examples of this cyclic conjugated diene compound include cyclopentadiene, methylcyclopentadiene, ethylcyclopentadiene, n-propylcyclopentadiene, isopropylcyclopentadiene, 1,3-cyclohexadiene, methyl-1,3-cyclohexadiene, ethyl-1,3-cyclohexadiene, n-propyl-1,3-cyclohexadiene and isopropyl-1,3-cyclohexadiene. Above all, cyclopentadiene, methylcyclopentadiene, 1,3-cyclohexadiene and methyl-1,3-cyclohexadiene are particularly preferable. In this connection, no particular restriction is put on the substitutional position of the alkyl group in the cyclic conjugated diene compound, and any substitutional position is acceptable.

In the process of the present invention, an aldehyde which can be used as another raw material contains an alkyl group having 1 to 3 carbon atoms at the third position of an acrolein represented by the general formula (I)

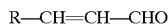  (I)

wherein R is an alkyl group having 1 to 3 carbon atoms. In the above-mentioned general formula (I), examples of the alkyl group having 1 to 3 carbon atoms represented by R include a methyl group, an ethyl group, an n-propyl group and an isopropyl group.

Examples of the aldehyde represented by the general formula (I) include 3-methylacrolein(crotonaldehyde), 3-ethylacrolein, 3-n-propylacrolein and 3-isopropylacrolein. Among others, crotonaldehyde is preferable from the viewpoints of the easiness of availability, reactivity, the usefulness of an obtained product and the like.

In the present invention, the above-mentioned cyclic conjugated diene compound is reacted with the aldehyde represented by the general formula (I) in accordance with the Diels-Alder reaction to prepare a cyclic unsaturated aldehyde, but at this time, it is necessary to use a solid acid as a catalyst. Examples of this solid acid include silica-alumina, silica-magnesia, alumina-boria, active terra abla, acidic terra abla, montmorillonite, solid phosphoric acid and a cation exchange resin, and above all, silica-alumina is preferable from the viewpoints of a catalytic activity and the like. The solid acid is preferably subjected to a drying treatment prior to its use in order to further improve the catalytic activity. No particular restriction is put on this drying treatment technique, and various techniques can be utilized. For example, there can be used a method in which the solid acid is heated at a temperature of about 150° to 250° C. for a period of about 1 to 20 hours, or a method in which the solid acid is dispersed in a suitable solvent, and water is then distilled off together with the solvent under heating. These solid acids may be used singly or in a combination of two or more thereof.

In the process of the present invention, no particular restriction is put on a molar ratio of the cyclic conjugated diene compound as the raw material to the aldehyde represented by the general formula (I), and the cyclic conjugated diene compound may be excessive or the aldehyde may be excessive, or both the compounds may be used in stoichiometric amounts. In addition, no particular restriction is put on a reaction system, and either of a fixed bed flow process and a batch process may be taken. As a technique of contacting the cyclic conjugated diene compound, the aldehyde and the catalyst, there can be used a method (1) which comprises bringing a previously prepared mixture of the cyclic conjugated diene compound and the aldehyde into contact with the catalyst, a method (2) which comprises adding the aldehyde to a mixture of the cyclic conjugated diene compound and the catalyst, or a method (3) which comprises adding the cyclic conjugated diene compound to a mixture of the aldehyde and the catalyst.

No particular restriction is put on a reaction temperature, but it can usually be selected in the range of 0° to 150° C. If this temperature is less than 0° C., a reaction rate is so slow as to be impractical, and on the other hand, if it is in excess of 150° C., the production of by products increases, so that a yield of the desired cyclic unsaturated aldehyde largely deteriorates on occasion. In view of the reaction rate and the yield, the reaction temperature is preferably in the range of 30° to 100° C. Furthermore, an amount of the catalyst depends on the kind of catalyst and the reaction temperature, and so it cannot sweepingly be decided. In the batch process, however, the amount of the catalyst is preferably in the range of 0.1 to 100% by weight, more preferably 1 to 50% by weight based on the weight of the raw material. On the other hand, in the fixed bed flow process, a WHSV (a weight hourly space velocity) is preferably in the range of 0.1 to 20 hr$^{-1}$, more preferably 0.2 to 10 hr$^{-1}$ from the viewpoint of a balance between productivity and conversion.

No particular restriction is put on a reaction pressure, but the reaction is usually carried out under atmospheric pressure. Furthermore, the reaction is usually done under non-solvent conditions, but if necessary, an inert solvent may suitably be used in the reaction.

In this way, the cyclic unsaturated aldehyde can be prepared in the high yield.

The process of the present invention can suitably be applied particularly in the case that 2-formyl-methylbicyclo [2,2,1]hepta-5-ene or 2-formyl-dimethylbicyclo-[2,2,1] hepta-5-ene is prepared by using cyclopentadiene or methylcyclopentadiene as the cyclic conjugated diene compound and using crotonaldehyde as the aldehyde represented by the general formula (I), or in the case that 2-formylmethylbicyclo[2,2,2]octa-5-ene or 2-formyl-dimethylbicyclo-[2,2,2]octa-5-ene is prepared by using 1,3-cyclohexadiene or methyl-1,3-cyclohexadiene as the cyclic conjugated diene compound and using crotonaldehyde as the aldehyde represented by the general formula (I).

Typical examples of the cyclic unsaturated aldehyde which is the above-mentioned product include 2-formyl-3-methylbicyclo[2,2,1]hepta-5-ene, 2-formyl-3,7-dimethylbicyclo[2,2,1]hepta-5-ene, 2-formyl-3- methylbicyclo[2,2,2]-octa-5-ene and 2-formyl-3,7-dimethylbicyclo[2,2,2]octa-5-ene.

Next, the present invention will be described in more detail with reference to examples, but the scope of the present invention should not be limited by these examples at all.

Comparative Example 1

In a 100 ml eggplant type flask were placed 40 g of a material mixture of crotonaldehyde and cyclopentadiene in a molar ratio of 2:1 and a magnetic stirrer, and stirring was then done at 20° C. on a water bath by the magnetic stirrer to carry out the Diels-Alder reaction. Reaction results after 3 hours, i.e., conversion based on cyclopentadiene and the selectivity of 2-formyl-3-methylbicyclo[2,2,1]hepta-5-ene on the basis of cyclopentadiene are shown in Table 1.

EXAMPLE 1

Reaction was carried out by the same procedure as in Comparative Example 1 except that 10 g of silica-alumina (N633L Catalyst, made by Nikki Chemical Co., Ltd.) was used as a catalyst in Comparative Example 1. Reaction results after 3 hours are shown in Table 1.

EXAMPLE 2

Reaction was carried out by the same procedure as in Comparative Example 1 except that 10 g of silica-alumina (N633HN Catalyst, made by Nikki Chemical Co., Ltd.) was used as a catalyst in Comparative Example 1. Reaction results after 3 hours are shown in Table 1.

EXAMPLE 3

Reaction was carried out by the same procedure as in Comparative Example 1 except that 10 g of montmorillonite (made by Aldorich Co., Ltd.) was used as a catalyst in Comparative Example 1. Reaction results after 3 hours are shown in Table 1.

EXAMPLE 4

Reaction was carried out by the same procedure as in Comparative Example 1 except that 10 g of solid phosphoric acid (E36Cl Catalyst, made by Nikki Chemical Co., Ltd.) was used as a catalyst in Comparative Example 1. Reaction results after 3 hours are shown in Table 1.

EXAMPLE 5

Reaction was carried out by the same procedure as in Comparative Example 1 except that 10 g of an active terra abla (Galeonite #136, made by Mizusawa Chemical Co., Ltd.) was used as a catalyst in Comparative Example 1. Reaction results after 3 hours are shown in Table 1.

Comparative Example 2

Reaction was carried out by the same procedure as in Comparative Example 1 except that 10 g of γ-alumina (N613N Catalyst, made by Nikki Chemical Co., Ltd.) was used as a catalyst in Comparative Example 1. Reaction results after 3 hours are shown in Table 1.

TABLE 1

| | | Reaction Results after 3 Hours | |
| --- | --- | --- | --- |
| | Kind of Catalyst | Conversion[1] (%) | Selectivity[2] (%) |
| Comp. Ex. 1 | — | 1 | 50 or less |
| Example 1 | Silica-alumina (N633L) | 64 | 98 |
| Example 2 | Silica-alumina (N633HN) | 28 | 97 |
| Example 3 | Montmorillonite | 22 | 97 |
| Example 4 | Solid phosphoric acid (E36C1) | 16 | 96 |
| Example 5 | Active terra abla (Galeonite #136) | 18 | 96 |
| Comp. Ex. 2 | γ-alumina (N613N) | 1 | 50 or less |

Notes:
[1] Conversion based on cyclopentadiene.
[2] Selectivity of 2-formyl-3-methylbicyclo[2,2,1]hepta-5-ene on the basis of cyclopentadiene.

Comparative Example 3

In a 2 liter stainless steel autoclave were placed 561 g (8 mol) of crotonaldehyde and 352 g (2.6 mol) of dicyclopentadiene, and reaction was then carried out at 175° C. for 4 hours, followed by distillation under reduced pressure, to obtain 503 g (3.7 mol) of 2-formyl-3-methylbicyclo[2,2,1]hepta-5-ene having a boiling point of 70° C./11 mmHg. Selectivity based on dicyclopentadiene was 79%.

EXAMPLE 6

In a 2 liter four-necked flask were placed 867 g (12.4 mol) of crotonaldehyde and 87 g of silica-alumina (N633L Catalyst, made by Nikki Chemical Co., Ltd.), followed by stirring at 60° C. In another 200 ml flask, 861 g (6.5 mol) of dicyclopentadiene was added dropwise to 100 g of a mineral oil heated to 250° C. over 10 hours to produce cyclopentadiene, and this cyclopentadiene was continuously added dropwise to the above-mentioned mixture of crotonaldehyde and silica-alumina to carry out reaction.

Next, the stirring of the reaction mixture was stopped and the silica-alumina catalyst was then allowed to precipitate, and the supernatant was drawn to obtain 1,627 g of a reaction mixture solution comprising 97 wt % of a desired product, i.e., 2-formyl-3-methylbicyclo[2,2,1]hepta-5-ene, 2 wt % of cyclopentadiene and 1 wt % of crotonaldehyde. The selectivity of 2-formyl-3-methylbicyclo[2,2,1]hepta-5-ene was 98% on the basis of crotonaldehyde.

The same experiment as described above was repeated 5 times by the use of this silica-alumina catalyst, but the selectivities of 2-formyl-3-methylbicyclo[2,2,1]hepta-5-ene on the basis of crotonaldehyde were all 98% or more, and the deterioration of the reaction results was not observed at all.

EXAMPLE 7

A stainless steel pressure flow type reaction tube having an inner diameter of 14 mm and a length of 240 mm was filled with 6 g of silica-alumina (N632L Catalyst, made by Nikki Chemical Co., Ltd.), and a material mixture of crotonaldehyde and cyclopentadiene in a molar ratio of 2:1 was fed thereto at a reaction tube inlet temperature of 40° C. and a WHSV of 3.0 hr$^{-1}$ to carry out reaction.

As a result, conversion based on cyclopentadiene was 98% or more, and the selectivity of 2-formyl-3-methylbicyclo[2,2,]hepta-5-ene was 99% or more on the basis of cyclopentadiene and 99% or more on the basis of crotonaldehyde. Furthermore, 120 g of the material mixture in total was fed, and at this time, the deterioration of reaction results was not observed at all.

EXAMPLE 8

Reaction was carried out by the same procedure as in Example 7 except that a material mixture of crotonaldehyde and cyclopentadiene in a molar ratio of 2:1 in Example 7 was replaced with a material mixture of crotonaldehyde and cyclopentadiene in a molar ratio of 1:1.2.

As a result, conversion based on crotonaldehyde was 98% or more, and the selectivity of 2-formyl-3-methylbicyclo[2,2,1]hepta-5-ene was 97% or more on the crotonaldehyde and 97% or more on the basis of cyclopentadiene.

Comparative Example 4

In a 100 ml eggplant type flask were placed 20 g of a material mixture of crotonaldehyde and cyclopentadiene in a molar ratio of 2:1, 1 g of a silica gel for column chromatography dried at 200° C. for 8 hours [Wako-Gel C-100, Wako Pure Chemical Industries] and a magnetic stirrer, and stirring was then done at 25° C. on a water bath by the magnetic stirrer to carry out the Diels-Alder reaction. Reaction results after 3 hours, i.e., conversion based on cyclopentadiene and the selectivity of 2-formyl-3-methylbicyclo[2;241]hepta-5-ene on the basis of cyclopentadiene shown in Table 2.

Comparative Example 5

Reaction was carried out by the same procedure as in Comparative Example 4 except that 1 g of a dried silica gel in Comparative Example 4 was replaced with an active alumina for column chormatography dried at 200° C. for 8 hours [made by Wako Pure Chemical Industries ]. Reaction results after 3 hours are shown in Table 2.

EXAMPLE 9

Reaction was carried out by the same procedure as in Comparative Example 4 except that 1 g of a dried silica gel in Comparative Example 4 was replaced with 1 g of a silica-aluminadried at 200° C. for 8 hours (N633L Catalyst, made by Nikki Chemical Co., Ltd.). Reaction results after 3 hours are shown in Table 2.

EXAMPLE 10

Reaction was carried out by the same procedure as in Comparative Example 4 except that 1 g of a dried silica gel in Comparative Example 4 was laced with 1 g of an active terra abla dried at 200° C. for 8 hours (Galeonite #136, made by Mizusawa Chemical Co., Ltd.). Reaction results after 3 hours are shown in Table 2.

TABLE 2

|  | Kind of[1] Catalyst | Reaction Results after 3 Hours | |
| --- | --- | --- | --- |
|  |  | Conversion[2] (%) | Selectivity[3] (%) |
| Comp. Ex. 4 | Silica gel (Wako-Gel C-100) | 4 | 72 |
| Comp. Ex. 5 | Active alumina | 6 | 71 |
| Example 9 | Silica-alumina (N633L) | 99 or more | 99 or more |
| Example 10 | Active terra abla (Galeonite #136) | 91 | 99 or more |

Notes:
[1]The catalysts were all dried at 200° C. for 8 hours.
[2]Conversion based on cyclopentadiene.
[3]Selectivity of 2-formyl-3-methylbicyclo[2,2,1]hepta-5-ene on the basis of cyclopentadiene.

As understood from a comparison between Example 2 and Example 9 as well as a comparison between Example 5 and Example 10, the dried solid acid catalysts can more improve a catalytic activity and can more heighten the conversion, as compared with the undry catalysts.

EXAMPLE 11

Reaction was carried out by the same procedure as in Example 9 except that a material of crotonaldehyde and cyclopentadiene in a molar ratio of 2:1 in Example 9 was replaced with a material of crotonaldehyde and methylcyclopentadiene in a molar ratio of 2:1. Reaction results after 3 hours are shown in Table 3.

EXAMPLE 12

Reaction was carried out by the same procedure as in Example 9 except that a material of crotonaldehyde and cyclopentadiene in a molar ratio of 2:1 in Example 9 was replaced with a material of crotonaldehyde and 1,3-cyclohexadiene in a molar ratio of 2:1 and a reaction temperature was 45° C. Reaction results after 3 hours are shown in Table 3.

COMPARATIVE EXAMPLE 5

Reaction was carried out by the same procedure as in Example 12 except that a catalyst in Example 12 was not used at all. Reaction results after 3 hours are shown in Table 3.

TABLE 3

|  | Reaction Results after 3 Hours | |
| --- | --- | --- |
|  | Conversion Based on Diene (%) | Selectivity Based on Diene (%) |
| Example 11 | 98 | 99 |
| Example 12 | 74 | 99 or more |
| Comp. Ex. 5 | 0 | — |

POSSIBILITY OF INDUSTRIAL UTILIZATION

According to a process of the present invention, a cyclic unsaturated aldehyde can efficiently be produced through the Diels-Alder reaction at a low cost without causing the corrosion of an apparatus and without requiring any treatment after the reaction. Therefore, the process of the present invention is industrially very advantageous.

The cyclic unsaturated aldehydes obtained by the process of the present invention are useful as, for example, the raw materials of traction oils and unsaturated polyester resins, modifiers for phenolic resins, and functional chemical products such as monomers for functional resins.

We claim:

1. A process for producing a cyclic unsaturated aldehyde which, which comprises the step of:

reacting a cyclic conjugated diene compound with an aldehyde of formula (I):

wherein R is a $C_{1-3}$-alkyl group, in the presence of a solid acid catalyst selected from the group consisting of silica-alumina, silica-magnesia, alumina-boria, active terra abla, acidic terra abla, montmorillonite, solid phosphoric acid and a cation exchange resin, in accordance with the Diels-Alder reaction.

2. The process according to claim 1 wherein the aldehyde represented by formula (I) is crotonaldehyde.

3. The process according to claim 1 wherein the cyclic conjugated diene compound contains a ring having 5 to 20 carbon atoms.

4. The process according to claim 1 wherein the cyclic conjugated diene compound is cyclopentadiene, methylcyclopentadiene, 1,3-cyclohexadiene or methyl-1,3-cyclohexadiene.

5. The process according to claim 1 wherein 2-formyl-methylbicyclo[2,2,1]hepta5-ene or 2-formyl-dimethylbicyclo[2,2,1]hepta-5-ene is prepared by using cyclopentadiene or methylcyclopentadiene as the cyclic conjugated diene compound and using crotonaldehyde as the aldehyde represented by formula (I).

6. The process according to claim 1 wherein 2-formyl-methylbicyclo [2,2,2]octa-5-ene or 2-formyl-dimethylbicyclo [2,2,2]octa-5-ene is prepared by using 1,3-cyclohexadiene or methyl-1,3-cyclohexadiene as the cyclic conjugated diene compound and using crotonaldehyde as the aldehyde represented by formula (I).

7. The process according to claim 1 wherein solid acid catalyst is dried.

8. The process according to claim 1 wherein the solid acid catalyst is silica-alumina.

9. The process according to claim 1 wherein said cyclic conjugated diene is cyclopentadiene, methylcyclopentadiene, ethylcyclopentadiene, n-propylcyclopentadiene, isopropylcyclopentadiene, 1,3-cyclohexadiene, methyl-1,3-cyclohexadiene, ethyl-1,3-cyclohexadiene, n-propyl-1,3-cyclohexadiene or isopropyl-1,3-cyclohexadiene.

10. The process according to claim 1, wherein the catalyzed reaction is conducted at a temperature of 150°–250° C. for a period of 1 to 20 hours.

* * * * *